(12) United States Patent
Katz et al.

(10) Patent No.: US 10,327,744 B2
(45) Date of Patent: Jun. 25, 2019

(54) ASSISTIVE MANUAL ZEROING VISUALIZATION

(71) Applicant: BIOSENSE WEBSTER (ISRAEL) LTD., Yokneam (IL)

(72) Inventors: Natan Sharon Katz, Kiryat Bialik (IL); Aharon Turgeman, Zichron Ya'acov (IL); Doron Moshe Ludwin, Haifa (IL); Ronen Krupnik, Karmiel (IL)

(73) Assignee: BIOSENSE WEBSTER (ISRAEL) LTD, Yokneam (IL)

( * ) Notice: Subject to any disclaimer, the term of this patent is extended or adjusted under 35 U.S.C. 154(b) by 888 days.

(21) Appl. No.: 14/315,408

(22) Filed: Jun. 26, 2014

(65) Prior Publication Data
US 2015/0374448 A1  Dec. 31, 2015

(51) Int. Cl.
| A61B 17/00 | (2006.01) |
| A61B 18/14 | (2006.01) |
| A61B 34/20 | (2016.01) |
| A61B 90/00 | (2016.01) |
| A61B 18/00 | (2006.01) |

(52) U.S. Cl.
CPC .... *A61B 17/00234* (2013.01); *A61B 18/1492* (2013.01); *A61B 34/20* (2016.02); *A61B 90/06* (2016.02); *A61B 2017/00243* (2013.01); *A61B 2017/00725* (2013.01); *A61B 2018/00357* (2013.01); *A61B 2018/00577* (2013.01); *A61B 2018/00839* (2013.01); *A61B 2034/2051* (2016.02); *A61B 2034/2065* (2016.02); *A61B 2090/064* (2016.02); *A61B 2090/065* (2016.02); *A61B 2090/374* (2016.02)

(58) Field of Classification Search
CPC ............ A61B 90/06; A61B 2034/2065; A61B 2090/065; A61B 2090/374; A61B 2017/00725; A61B 2018/00357; A61B 2018/00839
See application file for complete search history.

(56) References Cited

U.S. PATENT DOCUMENTS

| 6,226,542 B1 | 5/2001 | Reisfeld |
| 6,241,724 B1 | 6/2001 | Fleischman |
| 6,301,496 B1 | 10/2001 | Reisfeld |

(Continued)

FOREIGN PATENT DOCUMENTS

| EP | 2449996 A2 | 9/2012 |
| EP | 2574278 A2 | 3/2013 |

(Continued)

OTHER PUBLICATIONS

EP15173886—Expanded European Search Report dated Nov. 5, 2015.
U.S. Appl. No. 14/010,697, filed Aug. 27, 2013.
Chinese Office Action dated Sep. 4, 2018.

*Primary Examiner* — Amanda Lauritzen Moher
*Assistant Examiner* — Katherine M McDonald
(74) *Attorney, Agent, or Firm* — Louis J. Capezzuto

(57) ABSTRACT

A probe having a contact force sensor is inserted into a cardiac chamber and an image of the blood pool is generated. A portion of the blood pool is removed from the image to retain a remaining portion of the blood pool. A determination is made that the distal segment of the probe is within the remaining portion of the blood pool, and responsively to the determination the contact force sensor is manually zeroed.

9 Claims, 5 Drawing Sheets

(56) References Cited

U.S. PATENT DOCUMENTS

| | | |
|---|---|---|
| 6,695,808 B2 | 2/2004 | Tom |
| 6,814,733 B2 | 11/2004 | Schwartz |
| 6,892,091 B1 | 5/2005 | Ben Haim |
| 6,915,149 B2 | 7/2005 | Ben Haim |
| 6,997,924 B2 | 2/2006 | Schwartz |
| 7,156,816 B2 | 1/2007 | Schwartz |
| 7,536,218 B2 | 5/2009 | Govari |
| 7,756,576 B2 | 7/2010 | Levin |
| 9,259,290 B2 | 2/2016 | Jenkins et al. |
| 2007/0100332 A1 | 5/2007 | Paul |
| 2008/0172049 A1 | 7/2008 | Bredno et al. |
| 2008/0275465 A1 | 11/2008 | Paul |
| 2008/0288038 A1 | 11/2008 | Paul |
| 2009/0088629 A1* | 4/2009 | Groszmann .............. A61B 6/12 600/424 |
| 2012/0108988 A1 | 5/2012 | Ludwin |
| 2012/0158011 A1 | 6/2012 | Sandhu et al. |
| 2013/0165915 A1 | 6/2013 | Thiel et al. |
| 2015/0045647 A1* | 2/2015 | Katz ................... A61B 6/5205 600/409 |
| 2016/0367318 A1 | 12/2016 | Van der Weide et al. |

FOREIGN PATENT DOCUMENTS

| | | |
|---|---|---|
| WO | WO 2004107273 | 12/2004 |
| WO | WO 2012153231 | 11/2012 |

* cited by examiner

ASSISTIVE MANUAL ZEROING VISUALIZATION

BACKGROUND OF THE INVENTION

1. Field of the Invention

This invention relates to cardiac catheterization. More particularly, this invention relates to determination of contact of a catheter with cardiac tissue.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey radiofrequency energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

Impedance-based methods for assessing catheter-tissue contact that are known in the art typically rely on measurement of the magnitude of the impedance between an electrode on the catheter and a body-surface electrode. When the magnitude is below some threshold, the electrode is considered to be in contact with the tissue. This sort of binary contact indication may be unreliable, however, and is sensitive to changes in the impedance between the body-surface electrode and the skin.

U.S. Patent Application Publication Nos. 2008/0288038 and 2008/0275465, both by Sauarav et al., which are herein incorporated by reference, describe an electrode catheter system, which may comprise an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

U.S. Patent Application Publication No. 2013/0172875 to Govari et al., entitled "Contact Assessment Based on Phase Measurement", which is herein incorporated by reference, describes displaying intra-operative phase determinations of an electrical current passing between the ablation electrode and another electrode as an indicator of contact force between an ablation electrode and target tissue.

Today contact force catheters are commercially available, for example the THERMOCOOL® SMARTTOUCH™ Catheter, produced by Biosense Webster, Inc., 3333 Diamond Canyon Road, Diamond Bar, Calif. 91765.

SUMMARY OF THE INVENTION

There is provided according to embodiments of the invention a method, which is carried out by inserting a probe having a contact force sensor into a cavity in a body of a subject, the cavity having a blood pool and an endocardial surface, generating an image of the blood pool, removing a portion of the blood pool from the image to retain a remaining portion of the blood pool thereon, making a determination from the image that the distal segment of the probe is within the remaining portion of the blood pool, and responsively to the determination manually zeroing the contact force sensor.

According to one aspect of the method, the removed portion of the blood pool is adjacent the endocardial surface.

According to a further aspect of the method, the removed portion of the blood pool is adjacent another probe.

According to an additional aspect of the method, boundaries of the remaining portion of the blood pool are 3 mm from another probe in the cavity and 10 mm from the endocardial surface.

According to a further aspect of the method, boundaries of the remaining portion of the blood pool are 6 mm from another probe in the cavity and 13 mm from the endocardial surface.

There is further provided according to embodiments of the invention a method that is carried out by inserting a probe having a contact force sensor into a cavity in a body of a subject, the cavity having a blood pool and an endocardial surface. The method is further carried out by generating a first image of the blood pool, generating a second image to define an excluded region of the blood pool, generating subtraction images by subtracting the second image from the first image to define a zero-qualified region of the blood pool, and while generating the subtraction images navigating the probe within the cavity, until the distal portion is within the zero-qualified region.

Another aspect of the method includes making a determination from the subtraction images that the distal portion is within the zero-qualified region, and responsively to the determination enabling manual zeroing of the contact force sensor.

According to still another aspect of the method, a boundary of the other excluded region is at least 6 mm from another probe.

According to an additional aspect of the method, the first image and the subtraction images include the other probe.

There is further provided according to embodiments of the invention an apparatus, including a probe, configured for insertion into a body cavity having a blood pool, the probe including a contact force sensor for measuring a force applied to the contact force sensor and location sensors for detecting a location of the probe in the body cavity, and a processor, which is configured to receive a plurality of measurements from the contact force sensor. The processor is operative for generating an image of the blood pool, removing a portion of the blood pool from the image to retain a remaining portion of the blood pool thereon, and presenting a location of a distal segment of the probe on the image.

According to yet another aspect of the apparatus, the processor is operative for making a determination from the image that the distal segment of the probe is within the remaining portion of the blood pool, and responsively to the determination enabling manual zeroing of the contact force sensor.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

Figure 1:
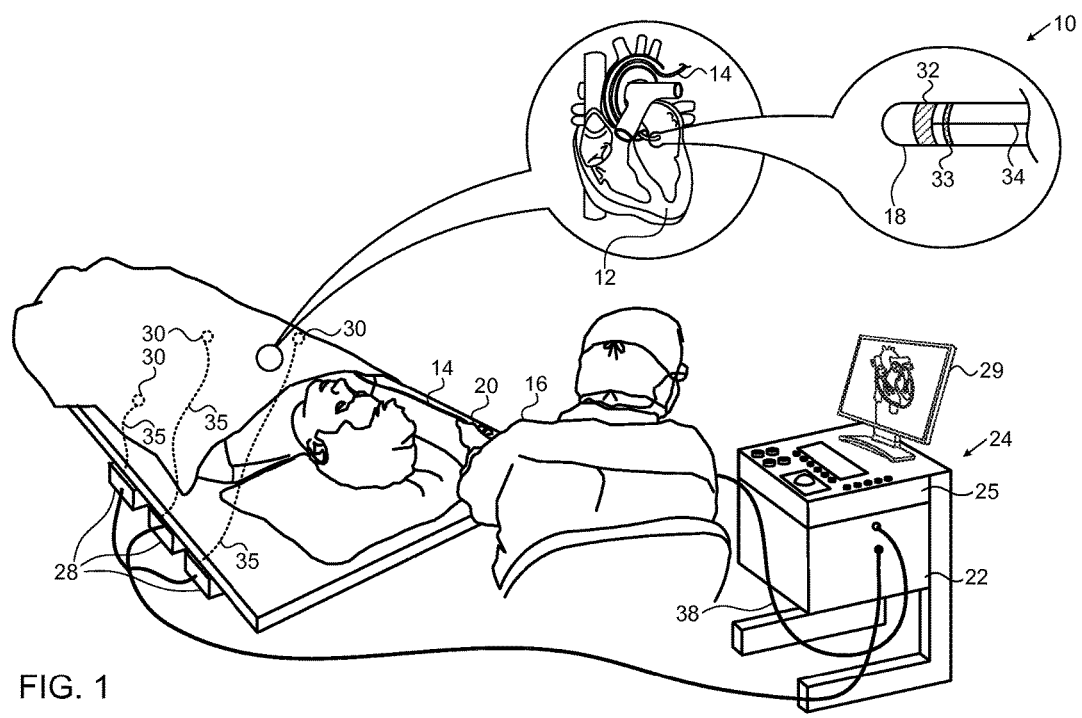
FIG. 1 is a pictorial illustration of a system for performing medical procedures in accordance with an embodiment of the invention.

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

In a medical ablation procedure, such as ablation of heart tissue, it is extremely useful to be able to measure the force applied to the tissue while the tissue is being ablated. This is because the force applied is a key parameter governing the amount of tissue ablated for a given ablation energy input to the tissue. The ablation is typically provided by a probe comprising an ablation electrode at its distal end. To accurately measure a force exerted by the distal tip on the endocardium, the force sensor incorporated into the distal end of the probe is typically calibrated to a "zero level," also referred to herein as a baseline. The baseline is determined from measurements generated by the force sensor when the distal tip has minimal contact with any surface (and therefore there is essentially no effective force exerted on the distal tip). The baseline may be determined using the techniques disclosed in U.S. Patent Application Publication No. 2012/0108988 to Ludwin et al., which is herein incorporated by reference. Once the baseline is identified, the measurements from the force sensor can be used to provide a value of the force exerted.

But such force sensors known in the art typically drift. Even if the force exerted on the sensor is constant, readings from the sensor change. Such drift may be compensated for by zeroing the sensor periodically, typically before applying ablation energy. However, the zeroing of the sensor should only be applied if the sensor is not contacting or in proximity to tissue or other catheters, i.e., the sensor is in a state where the force on it is effectively zero.

The force sensor is assumed to be in a zeroed state if over at least a predetermined interval of time force readings from the sensor change by less than a predetermined force limit. To ensure that the sensor is in the zeroed state, the probe having the force sensor is typically also assumed to change its location during the predetermined time interval by more than a predetermined location threshold.

Commonly assigned application Ser. No. 14/010,697, entitled "Determining Non-Contact State for a Catheter", whose disclosure is herein incorporated by reference, teaches how to detect a zeroed state for the sensor, and to calibrate a zero-force point for the force sensor. In order to auto-zero the sensor, received signals from the sensor are checked to detect a situation wherein the sensor is in a first zeroed state, then in a non-zeroed state (such as if the sensor indicates it is touching tissue), and then in a second zeroed state. Once such a situation is detected, force readings from the second zeroed state may be used as calibration values that zero the sensor.

The sensor is in a zeroed state where the force on it is effectively zero (such a state is typically achieved if the sensor is surrounded by blood in the heart chamber, and is not contacting a heart wall and the probe is not in proximity to another probe. Changes in proximity between probes may reduce the accuracy of the calibration values referred to above. In such cases, a probe may be assumed to be in the zeroed state if, in addition to the force condition described above, a measured value of the change in proximity to another probe is less than a predetermined proximity change threshold. In general, there is a high probability of accurately auto-zeroing the sensor when the sensor does not contact tissue. In addition, there is an extremely high probability of not auto-zeroing the sensor when the sensor does contact tissue.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

During the procedure, contact force between the distal tip 18 or ablation electrode 32 and the wall 37 may be measured using a position sensor in conjunction with the processor 22, or by any of the other techniques described above for verifying physical electrode contact with the target tissue.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images that are described below.

Figure 2:
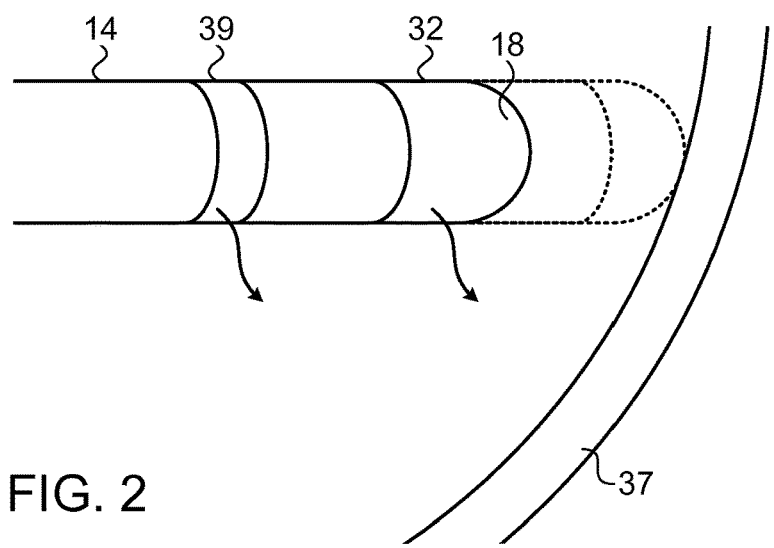
FIG. 2 is a schematic drawing of the distal portion of the catheter shown in FIG. 1 that includes a contact force sensor that can be adjusted in accordance with an embodiment of the invention.

Reference is now made to FIG. 2, which is a schematic drawing of the distal portion of catheter 14 showing contact force sensor 39. The figure shows and a first position (defined by solid lines) in which the distal tip 18 is not in contact with the endocardial surface of wall 37. In this position the signal from the sensor 39 can be accurately zeroed (provided no other catheter is nearby) A second position, defined by broken lines, illustrates a contacting relationship between the distal tip 18 and the wall 37. In the latter condition, the signal from the sensor 39 cannot be accurately zeroed.

Reverting to FIG. 1, operator-assisted contact force zeroing is often more comforting to the operator than the above-noted auto-zeroing techniques, as he has a degree of control. Confidence on the part of the operator in the accuracy of the zeroed state is important, as inaccurate contact force measurements may result in serious complications, such as perforation of the wall and hemopericardium. This is particularly true when ablating tissue in right atrium, the thinnest of the cardiac chambers. To assure the operator that the contact force measurement is accurate, an operator-assisted zeroing visualization procedure is executed, e.g., by the processor 22. A map of the heart 12 is displayed on the monitor 29, and regions of the map that qualify for manual zeroing of the catheter become highlighted. The operator navigates the catheter 14 such that it is located in a highlighted region. As noted above, the regions qualifying for zeroing in the blood pool are not too close (less than 3 mm) to the endocardial surface or to other catheters. Closer proximity than 3 mm may produce system inaccuracies and trigger shaft proximity interference mechanisms found in some catheters. The blood pool may be defined by exploiting the algorithms described in the above-mentioned application Ser. No. 14/010,697. When more than one catheter is present, the algorithms may be modified by those skilled in the art to exclude their neighborhoods from the highlighted areas. Moreover, It is desirable to provide 3 mm safety margins as mentioned above in the definition of the blood pool and proximity detection in order to exclude additional regions, which may be problematic due to limitations in catheter localization accuracy.

The operator-assisted manual zeroing visualization procedure may alert the operator or even disable his ability to perform manual contact force zeroing when the catheter is detected, e.g., by the processor 22 in areas that are not suitable for zeroing, i.e., are not highlighted on the map displayed on the monitor 29.

Figure 3:
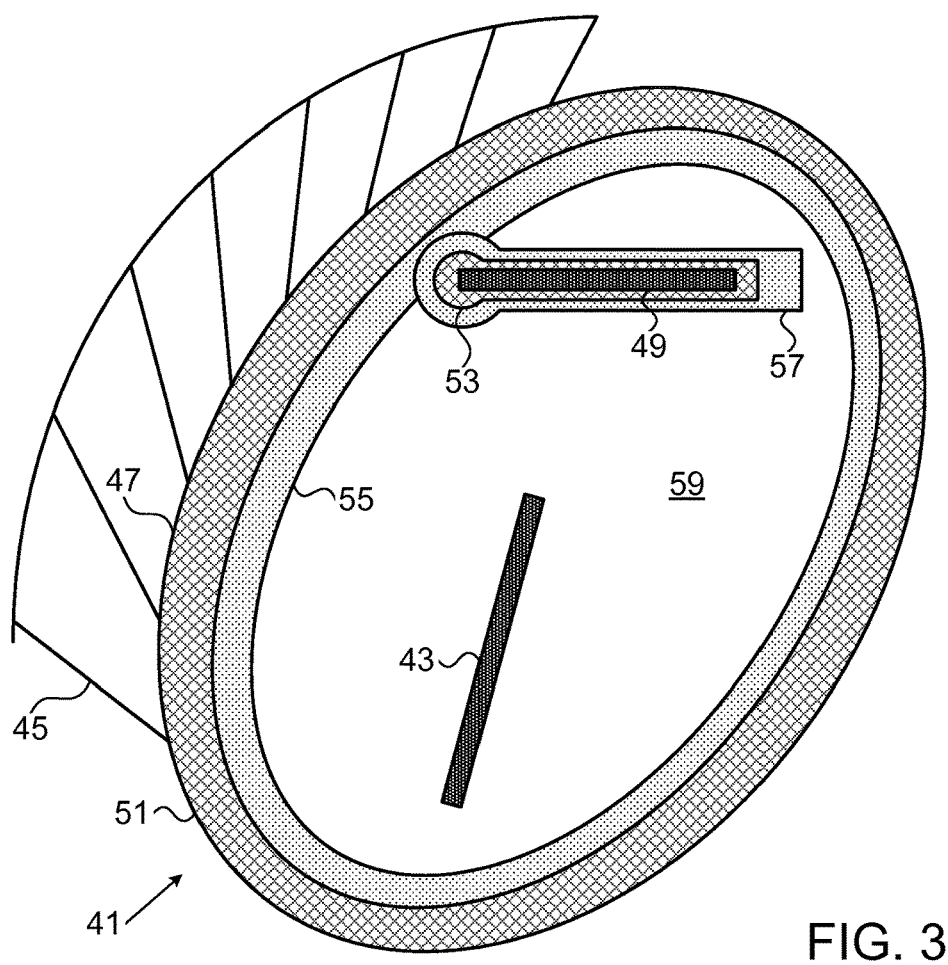
FIG. 3 is a schematic diagram of a cardiac chamber in accordance with an embodiment of the invention.

Reference is now made to FIG. 3, which is a schematic diagram of a cardiac chamber 41 illustrating zones varying in suitability for manual contact force zeroing, in accordance with an embodiment of the invention. A catheter 43 in the chamber 41 requires contact force zeroing. The chamber 41 is defined by myocardial wall 45 and an endocardial surface 47. As noted above zeroing is not reliable if performed when the catheter is too close to the endocardial surface 47 or another catheter 49. The catheter 43 must not be within a first exclusion zone 51 that extends from the endocardial surface 47 into the blood pool of the chamber 41. As noted above, the exclusion zone 51 is typically 10 mm wide. Moreover, the catheter 43 must not be within a second exclusion zone 53 about the catheter 49. The exclusion zone 53 is typically 3 mm wide. When the catheter 43 is not within the exclusion zones 51, 53 it is possible to manually zero the contact force sensor. However it is preferable to provide additional safety zones 55, 57 as buffers about the exclusion zones 51, 53, respectively. The zones 55, 57 are typically 3 mm thick. A careful operator will not manually zero the contact force sensor when the catheter 43 is within the zones 55, 57, but will require that the catheter 43 be in a region 59 of the blood pool that is not within any of the zones 51, 53, 55, 57. The safe boundaries of the region 59 are thus 13 mm from the endocardial surface 47 and 6 mm from the catheter 49.

Figure 4:
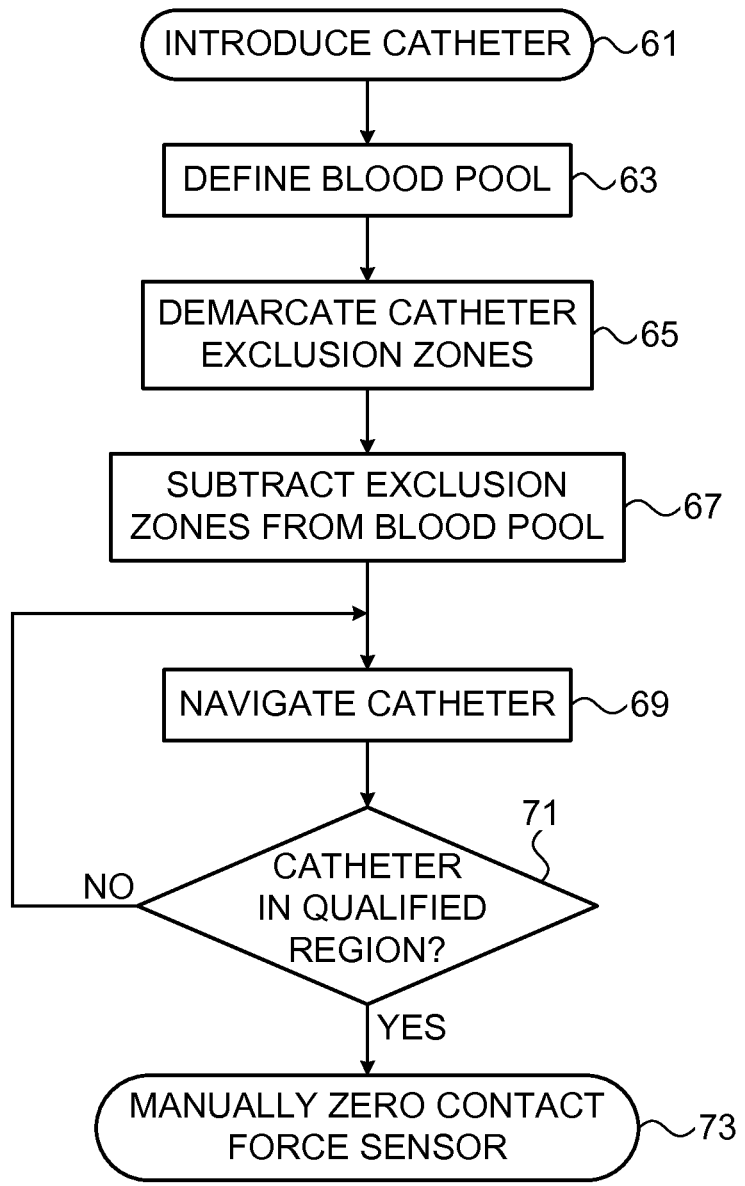
FIG. 4 is a flow chart of a method of assistive manual contact force zeroing in a cardiac catheter in accordance with an embodiment of the invention.

Reference is now made to FIG. 4, which is a flow chart of a method of assistive manual contact force zeroing in a cardiac catheter, in accordance with an embodiment of the invention. The process steps are shown in a particular linear sequence in FIG. 4 for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the process.

At initial step 61 catheterization of a cardiac chamber is accomplished conventionally. A contact force catheter and optionally other catheters are introduced into a cardiac chamber.

Next, at step 63, a definition of the blood pool of the cardiac chamber is displayed as a first image.

Next, at step 65, The blood pool is redrawn to exclude a first region of the blood pool adjacent the endocardial surface of the cardiac chamber, referred to herein as a first excluded region. Typically, the first excluded region is about 10 mm away from any tissue due to contraction and expansion of the heart. Furthermore, each catheter within the chamber other than the contact force catheter is surrounded by a respective spherical proximity zone, which constitutes a second excluded region. Steps 63, 65 may be accomplished using the procedures described in the above-mentioned application Ser. No. 14/010,697. A second image may be generated in which the first excluded region and the second included regions are highlighted.

Next, at step 67, the first excluded region and the second exclusion regions defined on the second image in step 65 are subtracted from the first image that was produced in step 63, using standard image processing routines. A subtraction image is generated. The portion of the blood pool that remains on the subtraction image is referred to herein as a zero-qualified region, because it is suitable for manually zeroing the contact force sensor.

Referring again to FIG. 4, next, at step 69, the catheter is navigated by the operator and new images of the distal portion of the catheter and the blood pool are generated. The zero-qualified region may be highlighted to assist the operator.

Next, at decision step 71, it is determined by evaluation of the new images if the catheter is in the zero-qualified region that was established at step 67. If the determination is negative, then control returns to step 69 and the catheter is repositioned.

If the determination at decision step 71 is affirmative then control proceeds to final step 73. The operator zeroes the contact force sensor, and the procedure ends.

Figure 5:
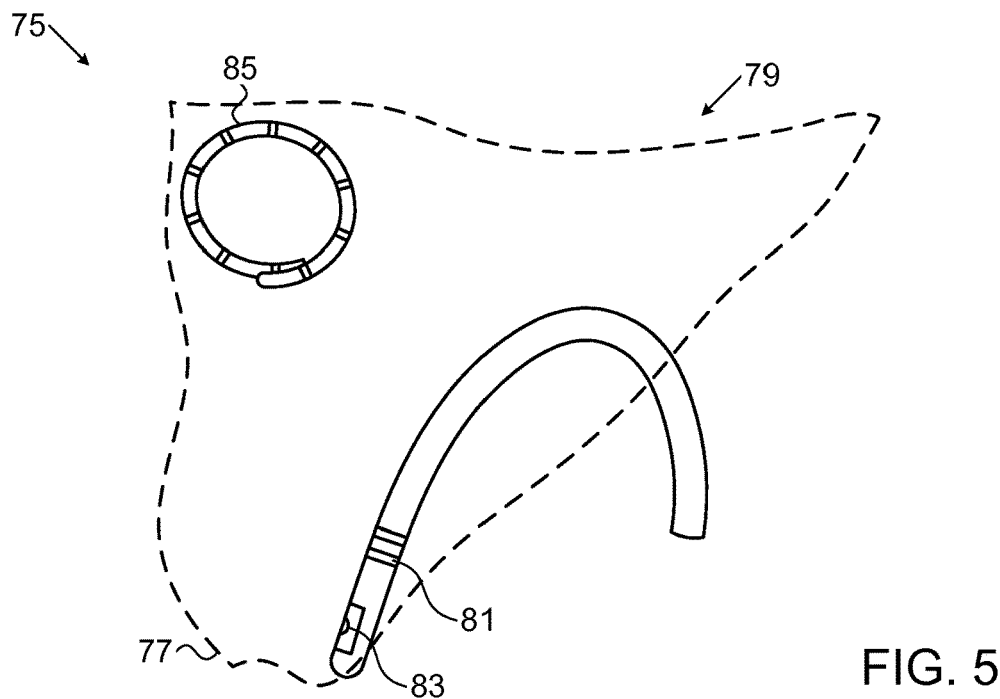
FIG. 5 is a screen display illustrating a phase of the method of FIG. 4 in accordance with an embodiment of the invention.

Reference is now made to FIG. 5, which is a screen display 75 obtained after completion of initial step 61 (FIG. 4) in accordance with an embodiment of the invention. The screen display 75 shows blood pool 77 of a cardiac chamber 79 in which is found an ablation catheter 81 having a contact force sensor 83 at its distal end. A mapping catheter 85 is also present in the cardiac chamber 79.

Figure 6:
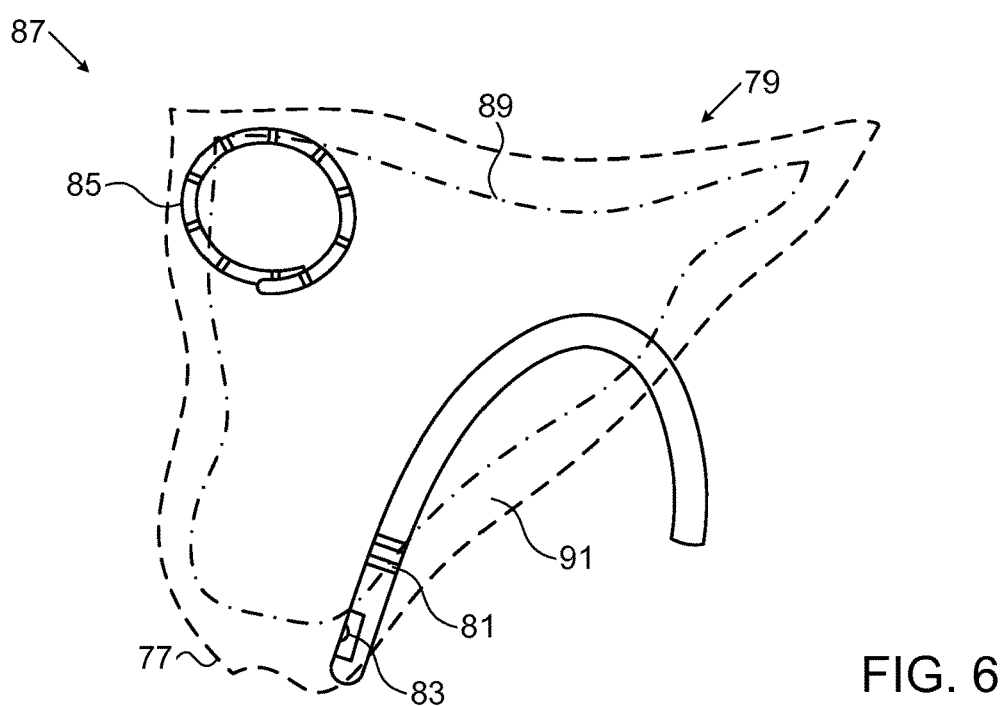
FIG. 6 is a screen display illustrating a phase of the method of FIG. 4 in accordance with an embodiment of the invention.

Reference is now made to FIG. 6, which is a screen display 87 obtained after completion of step 63 in accordance with an embodiment of the invention. The initial definition of the blood pool is highlighted and demarcated by a solid line 89. Portions of the blood pool 77 in a zone 91 external to the line 89 define the above-described first excluded region. Such portions are not suitable for contact force zeroing, as they are too close to the endocardial surface. It will be appreciated that while the screen display 87 is an exemplary 2-dimensional projection of a 3-dimensional object, the display can be varied, to represent many views and projections in order to enable the operator to appreciate the location of the catheter anywhere within the interior of the cardiac chamber 79.

Figure 7:
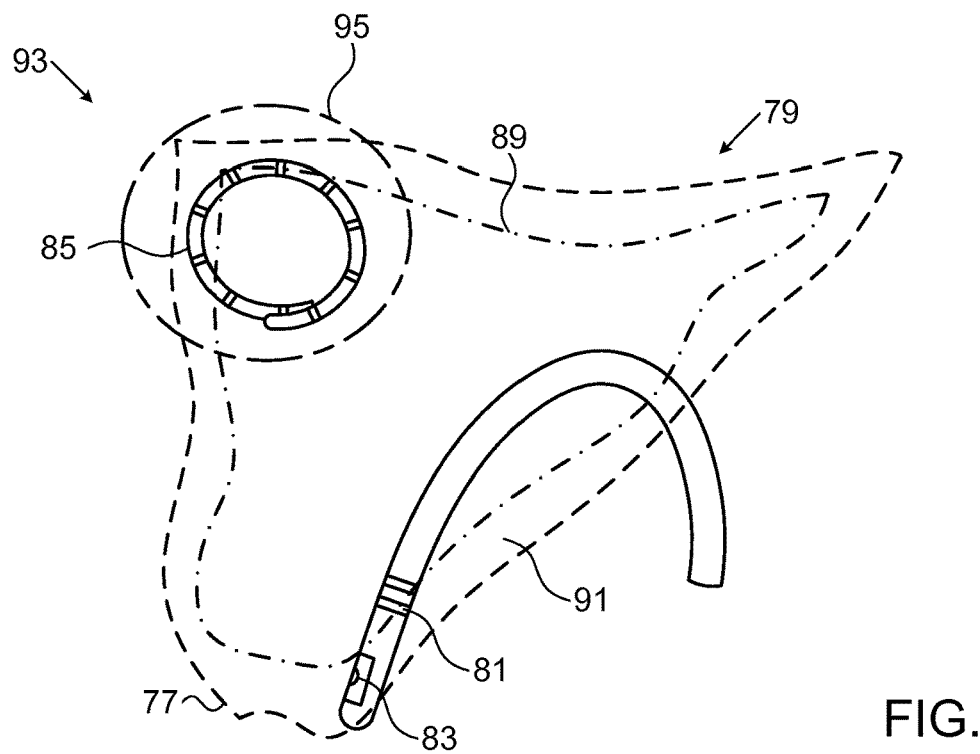
FIG. 7 is a screen display illustrating a phase of the method of FIG. 4 in accordance with an embodiment of the invention.

Reference is now made to FIG. 7, which is a screen display 93 obtained after completion of step 65, in accordance with an embodiment of the invention. A spherical zone, which appears roughly as a circle 95 in the 2-dimensional projection of FIG. 7 demarcates the above-described second excluded region about the catheter 85. Although not shown in FIG. 7, respective exclusion regions of this sort would be demarcated about all other catheters found in the cardiac chamber 79 (other than the contact force catheter 81).

Figure 8:
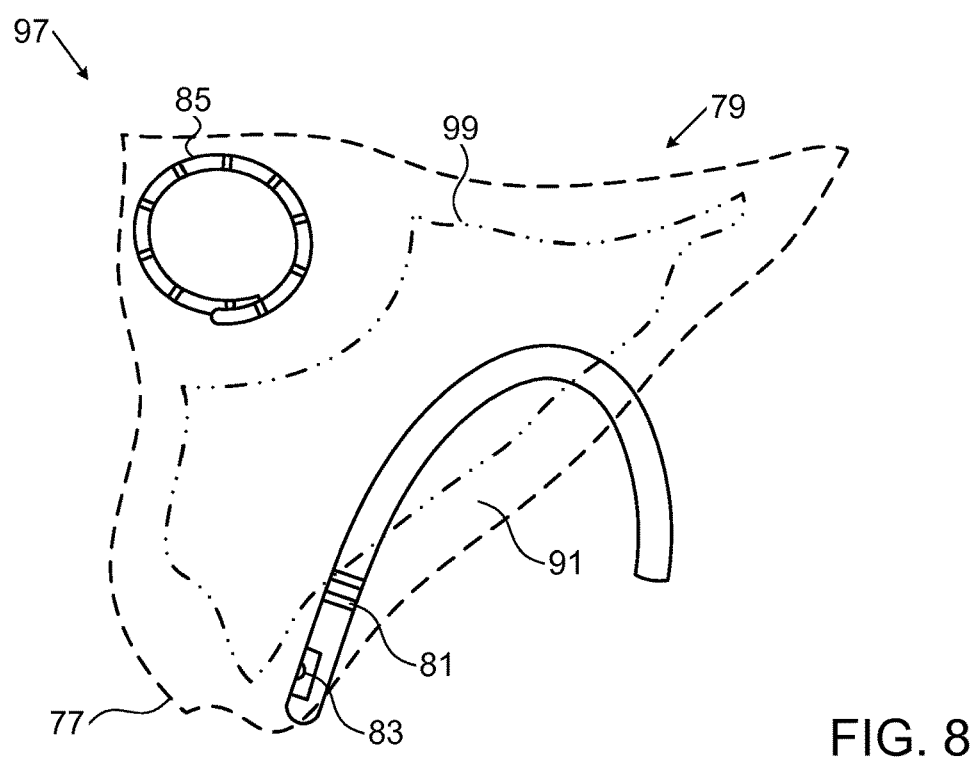
FIG. 8 is a screen display illustrating a phase of the method of FIG. 4 in accordance with an embodiment of the invention.

Reference is now made to FIG. 8, which is a screen display 97 of a subtraction image obtained after completion of step 67 in accordance with an embodiment of the invention. The remaining portion of the blood pool 77, outlined by solid line 99 represents the zero-qualified region in which contact force zeroing of the contact force sensor 83 can be accomplished with confidence.

The procedure shown in FIG. 4 is represented Listing 1 by pseudocode, which can be implemented on an image processor.

---
Listing 1
---

```
Create the chamber volume and draw all catheters in CatheterList
BloodPoolVolume = Find Blood pool( )
Mark BloodPoolVolume volume with color;
For each Catheter in CatheterList
    If Catheter not ContactForceCatheter then
        Mark catheter exclusion zone with VolumetricSphere
    End If
Next Catheter
Calculate ManualZeroSuggestion as
BloodPoolVolume − Union of VolumetricSpheres
```

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus, comprising:
a probe, configured for insertion into a body cavity having a blood pool and an endocardial surface of a patient and comprising a contact force sensor for measuring a force applied to the contact force sensor and location sensors for detecting a location of the probe in the body cavity; and
a processor, which is configured to receive a plurality of measurements from the contact force sensor and the location sensors, the processor configured to:
define the blood pool and generating an image of the body cavity showing the blood pool and the endocardial surface;
determine a first portion of the blood pool adjacent the endocardial surface to be removed from the image, the portion being a predetermined distance from the endocardial surface;
remove the first portion of the blood pool from the image to retain a remaining portion of the blood pool thereon;
regenerate the image to present the remaining portion of the blood pool and a location of a distal segment of the probe relative to the remaining portion on the image;
make a determination from the image that the distal segment of the probe is within the remaining portion of the blood pool; and
responsively to the determination enable manual zeroing of the contact force sensor.

2. The apparatus according to claim 1, wherein the predetermined distance from the endocardial surface determined by the processor comprises a 10 mm zone adjacent an endocardial surface of a heart.

3. The apparatus according to claim 1, wherein the predetermined distance from the endocardial surface determined by the processor comprises a 10-13 mm zone adjacent an endocardial surface of a heart.

4. The apparatus according to claim 1, wherein the processor is further configured to:
detect a location of a second probe in the body cavity; and
determine a second portion of the blood pool adjacent the second probe to be removed from the image, the portion being a predetermined distance from the second probe;
wherein both the first and second portions of the blood pool are removed from the image to retain the remaining portion of the blood pool thereon.

5. The apparatus according to claim 4, wherein the predetermined distance from the second probe determined by the processor is 3 mm in thickness.

6. The apparatus according to claim 4, wherein the predetermined distance from the second probe determined by the processor is 3-6 mm in thickness.

7. The apparatus according to claim 4, further comprising the second probe, wherein the image includes the second probe.

8. The apparatus of claim 1, wherein when the processor is further configured to:
determine that the distal segment of the probe is located outside the remaining portion of the blood pool; and
alert an operator that the probe is not located within the remaining portion of the blood pool.

9. The apparatus of claim 1, wherein the processor is further configured to:
determine that the distal segment of the probe is located outside the remaining portion of the blood pool; and
disable the ability of the operator to perform manual contact force zeroing.

* * * * *